(12) United States Patent
Boschetti

(10) Patent No.: US 7,670,592 B2
(45) Date of Patent: *Mar. 2, 2010

(54) POLYVINYL ALCOHOL MICROSPHERES, INJECTABLE SOLUTIONS AND THERAPEUTIC USES OF THE SAME

(75) Inventor: Egisto Boschetti, Croissy-sur-Seine (FR)

(73) Assignee: BioSphere Medical, S.A., Louvres (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/348,867

(22) Filed: Jan. 5, 2009

(65) Prior Publication Data

US 2009/0117196 A1 May 7, 2009

Related U.S. Application Data

(62) Division of application No. 10/692,785, filed on Oct. 27, 2003, now Pat. No. 7,591,993, which is a division of application No. 09/419,114, filed on Oct. 15, 1999, now Pat. No. 6,680,046.

(30) Foreign Application Priority Data

Oct. 16, 1998 (FR) .................................... 98 13019

(51) Int. Cl.
A61K 49/00 (2006.01)
(52) U.S. Cl. .................. 424/9.1; 424/489; 424/450; 424/1.11; 424/1.65
(58) Field of Classification Search .......... 424/1.11, 424/1.29, 1.65, 9.1, 400, 450, 489; 428/402, 428/402.2, 402.21, 402.24, 403
See application file for complete search history.

(56) References Cited

U.S. PATENT DOCUMENTS

| | | | |
|---|---|---|---|
| 3,919,411 A | 11/1975 | Glass et al. | |
| 4,268,495 A | 5/1981 | Muxfeldt et al. | |
| 4,306,031 A | 12/1981 | Itagaki et al. | |
| 4,314,032 A | 2/1982 | Murayama et al. | |
| 4,320,040 A | 3/1982 | Fujita et al. | |
| 4,350,773 A | 9/1982 | Itagaki et al. | |
| 4,367,323 A | 1/1983 | Kitamura et al. | |
| 4,657,553 A | 4/1987 | Taylor | |
| 4,680,171 A | 7/1987 | Shell | |
| 4,803,075 A | 2/1989 | Wallace et al. | |
| 4,863,972 A | 9/1989 | Itagaki et al. | |
| 4,999,188 A | 3/1991 | Solodovnik et al. | |
| 5,007,940 A | 4/1991 | Berg | |
| 5,028,332 A | 7/1991 | Ohnishi | |
| 5,092,883 A | 3/1992 | Eppley et al. | |
| 5,106,876 A | 4/1992 | Kawamura | |
| 5,114,577 A * | 5/1992 | Kusano et al. ............ 210/198.2 |
| 5,186,922 A | 2/1993 | Shell et al. | |
| 5,202,352 A | 4/1993 | Okada et al. | |
| 5,410,016 A | 4/1995 | Hubbell et al. | |
| 5,470,911 A | 11/1995 | Rhee et al. | |
| 5,550,188 A | 8/1996 | Rhee et al. | |
| 5,571,182 A | 11/1996 | Ersek et al. | |
| 5,578,709 A | 11/1996 | Woiszwillo | |
| 5,593,990 A | 1/1997 | D'Amato | |
| 5,624,685 A | 4/1997 | Takahashi et al. | |
| 5,629,327 A | 5/1997 | D'Amato | |
| 5,635,215 A * | 6/1997 | Boschetti et al. ............ 424/501 |
| 5,648,100 A * | 7/1997 | Boschetti et al. ............ 424/501 |
| 5,712,291 A | 1/1998 | D'Amato | |
| 5,752,974 A | 5/1998 | Rhee et al. | |
| 5,785,977 A | 7/1998 | Breithbarth | |
| 5,798,096 A | 8/1998 | Pavlyk | |
| 5,955,108 A | 9/1999 | Sutton et al. | |
| 6,060,582 A | 5/2000 | Hubbell et al. | |
| 6,165,193 A | 12/2000 | Greene, Jr. et al. | |
| 6,242,512 B1 * | 6/2001 | Figge et al. ................ 523/340 |
| 6,306,922 B1 | 10/2001 | Hubbell et al. | |
| 6,335,028 B1 | 1/2002 | Vogel | |
| 6,436,424 B1 | 8/2002 | Vogel | |
| 6,488,952 B1 | 12/2002 | Kennedy et al. | |
| 6,500,190 B2 | 12/2002 | Greene, Jr. et al. | |
| 6,537,569 B2 | 3/2003 | Cruise | |
| 6,565,885 B1 * | 5/2003 | Tarara et al. ................ 424/489 |
| 6,602,975 B2 | 8/2003 | Hubbell et al. | |
| 6,652,883 B2 | 11/2003 | Goupil et al. | |
| 6,660,301 B1 | 12/2003 | Vogel | |

(Continued)

FOREIGN PATENT DOCUMENTS

EP 0470569 2/1992

(Continued)

OTHER PUBLICATIONS

Barnes et al, Cytometry, 1999, vol. 36, No. 3, pp. 169-175.*

(Continued)

*Primary Examiner*—D L Jones
(74) *Attorney, Agent, or Firm*—Jones Day

(57) ABSTRACT

The present invention relates to microspheres useful for embolization which comprises polyvinylalcohol. The present invention also relates to an injectable suspension suitable for embolization which comprises the polyvinylalcohol microspheres and a suitable liquid carrier. The present invention further relates to a method for prophylactic or therapeutic embolization which comprises administering to a mammal an injectable suspension containing the polyvinylalcohol microspheres and a suitable liquid carrier. Finally, the present invention relates to a process for producing the polyvinylalcohol microspheres.

28 Claims, No Drawings

U.S. PATENT DOCUMENTS

| | | | |
|---|---|---|---|
| 6,676,971 | B2 | 1/2004 | Goupil et al. |
| 6,680,046 | B1 * | 1/2004 | Boschetti ............... 424/9.1 |
| 6,710,126 | B1 | 3/2004 | Hirt et al. |
| 6,790,456 | B2 | 9/2004 | Vogel |
| 6,911,219 | B2 | 6/2005 | Matson |
| 7,060,298 | B2 | 6/2006 | Vogel |
| 7,338,657 | B2 | 3/2008 | Vogel |
| 7,591,993 | B2 | 9/2009 | Boschetti |
| 2003/0211165 | A1 | 11/2003 | Vogel |
| 2004/0091425 | A1 | 5/2004 | Boschetti |
| 2004/0096514 | A1 | 5/2004 | Vogel |
| 2005/0025708 | A1 | 2/2005 | Vogel |
| 2005/0158393 | A1 | 7/2005 | Reb |
| 2006/0063732 | A1 | 3/2006 | Vogel |
| 2006/0251582 | A1 | 11/2006 | Reb |
| 2008/0033366 | A1 | 2/2008 | Matson |
| 2008/0039890 | A1 | 2/2008 | Matson |
| 2008/0118569 | A1 | 5/2008 | Vogel |
| 2008/0220077 | A1 | 9/2008 | Vogel |
| 2009/0117196 | A1 | 5/2009 | Boschetti |
| 2009/0186094 | A1 | 7/2009 | Vogel |

FOREIGN PATENT DOCUMENTS

| | | |
|---|---|---|
| EP | 1128816 B1 | 9/2001 |
| JP | 49108168 | 10/1974 |
| JP | 53050290 | 5/1978 |
| JP | 57128709 | 8/1982 |
| JP | 6056676 | 3/1994 |
| WO | WO 99/11196 | 11/1993 |
| WO | WO 98/16265 | 4/1998 |
| WO | WO 99/12577 | 3/1999 |

OTHER PUBLICATIONS

Bachtsi et al, Journal of Microencapsulation, 1995, vol. 12, No. 1, pp. 23-35.*

Hawley's 12th Edition, 1993, Condensed Chemical Dictionary by Richard J. Lewis, Sr., pp. 1058-1059.*

U.S. Appl. No. 12/534,070, filed Jul. 31, 2009, Vogel et al.

Bachtsi & Kiparissides, "An Experimental Investigation of Enzyme Release from Poly(vinyl alcohol) Crosslinked Mircospheres," *J Microencapsulation* 12(1):23-35 (1995).

Barnes et al., "Fluorescence imaging of single molecules in polymer microspheres," *Cytometry* 36:169-175 (1999).

Barton et al., "Embolization of bone metastases," *J. Vasc. Interv, Radiol.* 7:81-88 (1996).

Brown et al., "Synthese et copolymerisation de nouveaux monomeres acryliques diiodes et triodes," *Bulletin de la Societe Chimique de France*, No. 4. 839-847 (1986).

Boschetti, "Polyacrylamide Derivatives to the Service of Bioseparations," *J. Biochem. Biophys. Meth.* 19:21-36 (1989).

Dunn, "The peculiarities of polyvinyl alcohol," *Chemistry & Industry*, London, pp. 801-806 (1980).

Finch, "Properties and Applications," *Polyvinyl Alcohol*, p. 640, Wiley, New York (1973).

Flandroy et al., "Clinical Applications of Microspheres in Embolization and Chemoembolization: A Comprehensive Review and Perspectives," *In: Pharmaceutical Particulate Carriers in Medical Applications*, (Rolland, A., Ed., New York: Marcel Dekker, Inc.) 61: 321-366 (1993).

Hori et al., "A New Embolic Material: Superabsorbant Polymer Microspehre and Its Embolic Effectes." *J International Radiol* 11(3): 75-81 (1996) [English Translation; English translated Title: "Study on the Effect of Arterial Embolization with Super-absorbent Polymer"].

Hori et al., "A New Embolic Material: Superabsorbant Polymer Microspehre and Its Embolic Effectes." *J International Radiol* 11(3): 75-81 (1996) [Japanese].

Hori et al., "A study of development and practical uses of new arterial embolic materials (Super Water-absorbent Resins," *Innervision* 13:24 (1998).

Hori et al., "An Experimental Study of a New Embolic Material-Lipiodol Suspension of Water-Absorbent Particle," *Nippon Acta Radiologica* 53(1):50-56 (1993).

Hori et al., "Embolotherapy of Large Hepatocellular Carcinoma Using a New, Permanent, Spherical Embolic Material Without Anti-Neoplastic Agents," *Cardiovasc Intervent Radiol* 24 (Suppl 1) S203 (2001).

Hori et al., "Vessel Embolic Materials," *Intervent Radiol* 33:109-112 (1999).

Hori et al. "Study on the effect of arterial embolization with super-absorbant polymer" *Intervent. Radiol.* 11:1-11 (1996) (Japanese).

Hori et al. "Study on the effect of arterial embolization with super-absorbant polymer" *Intervent. Radiol.* 11:1-11 (1996) (English Translation).

Inoue et al., "Experimental Studies of Segmental Hepatic Artery Embolization with a Super Absorbent Embolic Agent," *Nippon Acta Radiologica* 50:1439-1441 (1990).

Iwase et al., "Hand-Assisted Laparoscopic Splenectomy for Idiopathic Thrombocytopenic Purpura During Pregnancy," *Surgical Laparoscopy, Endoscopy & Percutaneous Techniques* 11(1):53-56 (2001).

Iwase et al., "Laparoscopically Assisted Splenectomy following Preoperative Splenic Artery Embolization Using Contour Emboli for Myelofibrosis with Massive Splenomegaly," *Surgical Laparoscopy, Endoscopy & Percutaneous Techniques* 9(3):197-202 (1999).

Iwase et al., "Splenic Artery Embolization Using Contour Emboli before Laparoscopic or Laparoscopically Assisted Splenectomy," *Surgical Laparoscopy, Endoscopy & Percutaneous Techniques* 12(5):331-336 (2002).

Jiaqi, "A New Embolic Material: Super Absorbent Polymer (SAP) Microsphere and its Embolic Effects," *Nippon Acta Radiologica* 56(1):19-24 (1996) (Japanese).

Jiaqi, "A New Embolic Material: Super Absorbent Polymer (SAP) Microsphere and its Embolic Effects," *Nippon Acta Radiologica* 56(1):19-24 (1996) (English Translation).

Khankan et al., "Embolic Effects of Superabsorbent Polymer Microspheres in Rabbit Renal Model: Comparison with Trisacryl Gelatin Microspheres and Polyvinyl Alcohol," *Radiat Med* 22(6):384-390 (2004).

Kimura et al., "Transcatherterial Embolization of AVM in Pancreas," *Japanese J Clin Radiol* 43:311-314 (1998).

Kitamura et al., "Polymer with a High Water Absorption Property—Sumika Gel," *Sumitomo Chemical Special Issue.* 1-9 (1980) (Japanese).

Kitamura et al., "Polymer with a High Water Absorption Property—Sumika Gel," *Sumitomo Chemical Special Issue* 1-9 (1980) (English translation).

Kusano et al., "Low-Dose Particulate Polyvinylalcohol Embolization in Massive Small Artery Intestinal Hemorrhage. Experimental and Clinical Results," *Investigative Radiology* 22:388-292 (1987).

Lewis, "Hawley's Condensed Chemical Dictionary," 12th Edition, pp. 1058-1059 (1993).

Marvel et al., "End Group Structure of Polyvinyl Alcohol," *The Journal of the American Chemical Society* 65: 1710 (1943).

Marvel et al., "The Structure of Vinyl Polymers. II. Polyvinyl Alcohol," *The Journal of the American Chemical Society* 60:1045 (1938).

Mavligit et al., "Gastrointestinal Leiomyosarcoma Metastatic to the Liver," *Cancer* 75(8):2083-2088, (1995).

Merck Index, "Polysorbates," *12th Ed., Merck & Col., Inc.*, p. 1308 (1996).

Motohashi et al., "Superabsorbant Sumikagel®," *Sumitomo Chemistry* 35-47 (1985) [Japanese].

Motohashi et al, "Superabsorbant Sumikagelt®," *Sumitomo Chemistry* 35-47 (1985) [English translation].

Müller-Schulte & Brunner, "Novel Magnetic Microspheres on the Basis of Poly(vinyl alcohol) as Affinity Medium for Quantitative Detection of Glycated Haemoglobin," *J. Chromatography A* 711:53-60 (1995).

Norrby et al., "Angiogenesis: new aspects relating to its initiation and control," *APMIS* 105:417-437 (1997).

Leeds, "Vinyl Polymers (Alcohol)," *Encyclopedia of Chemical Technology*, Kirkothmer ed., 21 :353-368, Wiley-Interscience, New York, 2nd ed., (1970).

McDowell, et al., "Some Relationships between Polyvinyl Acetates and Polyvinyl Alcohols," *J. Am. Soc.* 62:415 (1940).

Osuga et al., "Management of Advanced Pelvic Bone Tumors by Transarterial Embolotherapy Using SAP-Microspheres. A Preliminary Report," *Cardiovasc Intervent Radiol* 22:S130 (1999).

Osuga et al., "Embolization of High Flow Arteriovenous Malformations: Experience with Use of Superabsorbent Polymer Microspheres," *J Vasc Intervent Radiol* 13(11):1125-1133 (2002).

Osuga et al., "A New Embolic Material: SAP-Microsphere," *Japanese Journal of Clinical Medicine* 59 Suppl 6:534-538 (2001).

Osuga et al., "Transarterial Embolization for Large Hepatocellular Carcinoma with Use of Superabsorbent Polymer Microspheres: Initial Experience," *J Vasc Intervvent Radiol* 13(9 Pt 1)929-934 (2002).

Repa et al., "Mortalities Associated with Use of a Commercial Suspension of Polyvinyl Alcohol," *Radiology* 170(2):395-399 (1989).

Rump et al., "Pharmacokinetics of intraarterial mitomycin C in the chemoembolisation treatment of liver metastases," *Gen. Pharmac.* 27(4): 669-671 (1996).

Thanoo et al., "Controlled release of oral drugs from cross-linked polyvinyl alcohol microspheres," *J Pharm. Pharmacol.* 45:16-20 (1993).

O'Reilly, "The preclinical evaluation of angiogenesis inhibitors," *Investigational New Drugs* 15:5-13(1997).

Tao et al., "Study on Microspheres for Embolization of Hepatic Artery," *Acta Pharmaceutica Sinica* 23(1):55-60 (1988) [Chinese].

Tao et al., "Study on Microspheres for Embolization of Hepatic Artery," *Acta Pharmaceutica Sinica* 23(1):55-60 (1988) [English Translation].

Thanoo et al., "Preparation and Properties of Barium Sulphate and Methyl Lothalamate Loaded Poly(vinyl Alcohol) Microspheres as Radiopaque Particulate Emboli," *J. Applied Biomaterials* 2:67-72 (1991).

Wakhloo et al., "Extended Preoperative Polyvinyl Alcohol Microembolization of Intracranial Meningiomas: Assessment of Two Embolization Techniques," *American Journal of Neurology* 14:571-582 (1993).

Ziegler et al., "Angiogenesis Research Enjoys Growth Spurt in the 1990s," *Journal of the National Cancer Institute* 88(12):786-788 (1996).

Zou et al., "Experimental Canine Hepatic Artery Embolization With Polyvinyl Alcohol Microsphere," *Zhonghua Fang She Xue Za Zhi* (*Chin. J. Radiol.*) 23(6):330-332 (1989) [Chinese].

Zou et al., "Experimental Canine Hepatic Artery Embolization With Polyvinyl Alcohol Microsphere," *Zhonghua Fang She Xue Za Zhi* (*Chin. J. Radio.*) 23(6):330-332 (1989) [English Translation].

Derdeyn et al.., "Polyvinyl Alcohol Particle Size and Suspension Characteristics," *AJNR Am. J. Neuroradiol.* 16(6):1335-1343 (1995).

Opposition of EP1128816B1—Notice of Opposition dated Dec. 22, 2004.

Opposition of EP1128816B1—Patentee Reply dated Aug. 10, 2005.

Opposition of EP1128816B1—Opponent Reply dated Feb. 21, 2006.

Opposition of EP1128816B1—Patentee Reply dated Mar. 8, 2007.

Opposition of EP1128816B1—Opponent Supplemental Reply dated May 2, 2007.

Opposition of EP1128816B1—EPO Summons to Attend Oral Proceedings and Preliminary Opinion dated May 14, 2007.

Opposition of EP1128816B1—Patentee Reply dated Oct. 10, 2007.

Opposition of EP1128816B1—Opponent Reply dated Oct. 10, 2007.

Opposition of EP1128816B1—Patentee Reply dated Dec. 3, 2007.

Opposition of EP1128816B1—Minutes of Oral Proceedings held Dec. 10, 2007; dated Dec. 27, 2007.

Opposition of EP1128816B1—EPO Interlocutory Decision dated Dec. 27, 2007.

Opposition of EP1128816B1—Opponent Notice of Appeal dated Feb. 21, 2008.

Opposition of EP1128816B1—Patentee Notice of Appeal dated Mar. 6, 2008.

Opposition of EP1128816B1—Opponent Reasons for Appeal dated May 1, 2008.

Opposition of EP 1128816B1—Experimental Report: cited as Document D23 in Opponent Appeal dated May 1, 2008.

Opposition of EP1128816B1—Patentee Reasons for Appeal dated May 6, 2008.

Opposition of EP1128816B1—Opponent Reply dated Nov. 5, 2008.

Opposition of EP1128816B1—Patentee Reply dated Nov. 26, 2008.

U.S. Appl. No. 09/419,114; (U.S. Patent No. 6,680,046) Office Action Dated Oct. 30, 2001.

U.S. Appl. No. 09/419,114; (U.S. Patent No. 6,680,046) Office Action Dated Jul. 3, 2002.

U.S. Appl. No. 09/419,114; (U.S. Patent No. 6,680,046) Notice of Allowability Dated Jul. 25, 2003.

U.S. Appl. No. 10/692,785; (U.S. Publ. No. 2004/0091425) Office Action Dated Nov. 16, 2005.

U.S. Appl. No. 10/692,785; (U.S. Publ. No. 2004/0091425) Office Action Dated Jun. 2, 2006.

U.S. Appl. No. 10/692,785; (U.S. Publ. No. 2004/0091425) Office Action Dated Oct. 30, 2006.

U.S. Appl. No. 10/692,785; (U.S. Publ. No. 2004/0091425) Interview Summary Dated Nov. 21, 2006.

U.S. Appl. No. 10/692,785; (U.S. Publ. No. 2004/0091425) Office Action Dated Jul. 12, 2007.

U.S. Appl. No. 10/692,785; (U.S. Publ. No. 2004/0091425) Office Action Dated Jan. 24, 2008.

U.S. Appl. No. 10/692,785; (U.S. Publ. No. 2004/0091425) Office Action Dated Sep. 4, 2008.

U.S. Appl. No. 10/692,785; (U.S. Publ. No. 2004/0091425) Notice of Allowability Dated Sep. 29, 2008.

\* cited by examiner

POLYVINYL ALCOHOL MICROSPHERES, INJECTABLE SOLUTIONS AND THERAPEUTIC USES OF THE SAME

CROSS-REFERENCE TO RELATED APPLICATIONS

This application is a divisional application of U.S. Ser. No. 10/692,785 filed Oct. 27, 2003, which is a divisional application of U.S. Ser. No. 09/419,114 (U.S. Pat. No. 6,680,046) filed Oct. 15, 1999, which claims priority to France application Serial No. 98-13019 filed Oct. 16, 1998.

1. FIELD OF INVENTION

The present invention relates to materials useful for embolization, methods for using the same for embolization and processes for producing such materials.

2. BACKGROUND OF THE INVENTION

Therapeutic vascular occlusions (embolizations) are used to prevent or treat certain pathological conditions in situ. Generally they are employed using catheters, under imagery control, to position particulate occlusion agents (emboli) in the circulatory system. Embolizations can be used in a variety of vessels and organs whether healthy or diseased; however, they are more commonly used in conditions such as, e.g., tumors, vascular malformations, hemorrhagic processes, etc. Notably, in the case of tumors, vascular occlusion can suppress pain, limit blood loss during surgical intervention following embolization or even bring on tumoral necrosis and avoid the necessity for surgical intervention. In the case of vascular malformations, embolization enables the blood flow to the "normal" tissues to be normalized, aids in surgery and limits the risk of hemorrhage. In hemorrhagic events or processes, vascular occlusion produces a reduction of blood flow, which promotes cicatrization of the arterial opening(s).

Furthermore, depending on the pathological conditions treated, embolization can be used for temporary as well as permanent objectives.

Embolization has been performed with a variety of solid materials such as small pieces of dura mater, irregular polyvinylalcohol particles, irregular gelatin particles, and more recently with crosslinked spherical hydrogel made from a polyacrylamide derivative and a crosslinked gelatin.

U.S. Pat. No. 5,635,215 discloses microspheres, comprising a hydrophilic acrylic copolymer coated with a cell adhesion promoter and a marking agent which are useful for embolization. U.S. Pat. No. 5,648,100 discloses an injectable solution for therapeutic embolization, comprising microspheres comprising a hydrophilic acrylic copolymer coated with a cell adhesion promoter and a marking agent. U.S. Pat. No. 5,648,100 also discloses a method for therapeutic embolization which comprises administering to a mammal the above injectable solution.

The most common material used to date in a variety of embolization applications is irregular polyvinylalcohol particles. However, these irregular polyvinylalcohol particles have numerous drawbacks, and can in certain circumstances even led to deaths. For example, Repa et al., *Radiology*, 1987, 170:395-399 discloses that two infants with symptomatic hepatic arteriovenous malformation (AVM) were treated with catheter embolization using commercially available polyvinylalcohol (IVALON particle suspensions from Laboratory Ingenor (Paris)). Both infants died soon after the AVM embolization. Further examination demonstrates that marked heterogeneity of particle size very probably contributed to the death of the infants. Indeed, these and other problems are associated with irregular polyvinylalcohol particles mostly due to their particle shapes. These problems make it difficult, or even dangerous in certain cases, to use irregular polyvinylalcohol particles in embolization.

Polyvinylalcohol products are commercially available from Target Therapeutics/Boston Scientific (CONTOUR), from Nycomed (IVALON, ULTRA-DRIVALON, and ULTRA-IVALON), from Cordis (TRUFILL) and from Cook (PVA). These polyvinylalcohol particles are known to be irregularly shaped particles. Generally, these polyvinylalcohol particles are sold as dry powders or saline suspensions. Despite their potential damage, irregular polyvinylalcohol particles have been used extensively. Examples of the use of irregular polyvinylalcohol particles are discussed below.

Kusano et al., *Invest. Radiol.*, 1987, 22:388-392, discloses low-dose particulate polyvinylalcohol embolization in animal and clinical studies. Polyvinylalcohol particles used in Kusano were IVALON obtained from Unipoint Laboratory, High Point, N.C., in the radiopaque form. Kusano discloses that low-dose large polyvinylalcohol particles (diameter at 590-1000 μm) are suitable as an embolic material for transcatheter occlusion of small intestinal hemorrhage in patients with certain diseases such as stress ulcer, surgical drain, anastomosis, tuberculous ulcer and nonspecific ulcer.

Rump et al., *Gen. Pharmac.*, 1996, 27(4):669-671, discloses pharmacokinetics of intraarterial Mitomycin C (MMC) in the chemo-embolization treatment of liver metastases. In Rump, hepatic branches of patients with primary colorectal cancer and liver metastases were embolized using irregular polyvinylalcohol particles (150-250 μm) before applying MMC.

Barton et al., *JVIR*, 1996, 7:81-88, discloses embolization of patients with bone metastases to prevent major blood loss during surgery, to reduce bone metastases, to reduce pain and to control heavy bleeding. Polyvinylalcohol foam particles (IVALON; DRIVALON 300-600 μm; Nycomed-Ingenor, Paris) were used in eight cases in Barton.

Wakhloo et al., *AJNR*, 1993, 14:571-582, discloses extended preoperative micro-embolization of intracranial meningiomas using 50-150 μm and 150-300 μm polyvinylalcohol particles. Wakhloo concluded from their study that embolization with 50-150 μm irregular polyvinylalcohol particles led to a higher percentage of effective tumor devascularization and tumor necrosis for intracranial meningiomas.

Given the interest in the use of polyvinylalcohol particles for embolization, there is a great need for a safe and effective method for its application. The present invention addresses these and other needs in the art.

3. SUMMARY OF THE INVENTION

Despite the risks and difficulties associated with the use of polyvinylalcohol particles in embolization, applicant has discovered surprisingly that microspheres made from crosslinked polyvinylalcohol are biocompatible, non-toxic and safe in embolization procedures. Accordingly, the present invention encompasses microspheres useful for embolization which comprise crosslinked polyvinylalcohol microspheres, injectable suspensions suitable for embolization which comprise the crosslinked polyvinylalcohol microspheres and a suitable liquid carrier, methods for prophylactic or therapeutic embolization using such injectable suspensions, and processes for producing the crosslinked polyvinylalcohol microspheres.

The invention described herein encompasses microspheres, having diameters ranging from about 10 μm to about 2,000 μm useful for embolization, which comprise crosslinked polyvinylalcohol. The microspheres of the present invention can be in the form of dry powder or hydrogel. In one embodiment, the present invention encompasses microspheres which comprise, in crosslinked and hydrogel form, about 0.5% to about 20% polyvinylalcohol by weight. In another embodiment, the present invention encompasses crosslinked polyvinylalcohol microspheres which further comprise a cell adhesion promoter, a marking agent, or both. In still another embodiment, the present invention encompasses polyvinylalcohol microspheres further comprising an anti-angiogenic agent.

The present invention also encompasses an injectable suspension suitable for prophylactic or therapeutic embolization, which comprises microspheres, having diameters ranging from about 10 μm to about 2,000 μm which comprise crosslinked polyvinylalcohol and a suitable liquid carrier. In a preferred embodiment, the present invention encompasses an injectable suspension wherein the microspheres comprise, in crosslinked and hydrogel form, about 0.5% to about 20% polyvinylalcohol by weight. In one embodiment, the microspheres in said injectable suspension have a uniform or narrow size range, wherein the difference in diameter between the microspheres is from about 0 μm to about 150 μm, preferably from about 0 μm to about 100 μm. In another embodiment, the present invention encompasses an injectable suspension wherein the crosslinked polyvinylalcohol microspheres further comprise a cell adhesion promoter, a marking agent or both. In still another embodiment, the present invention encompasses an injectable suspension wherein the polyvinylalcohol microspheres further comprise an anti-angiogenic agent.

The present invention additionally encompasses a method for prophylactic or therapeutic embolization in a mammal which comprises administering to said mammal an injectable suspension comprising an effective amount of microspheres, having diameters ranging from about 10 μm to about 2,000 μm, which comprise crosslinked polyvinylalcohol. An effective amount of said microspheres is generally the amount sufficient to occlude the vessel in question. In general, this amount is between a few dozen to a few hundred microspheres. In a preferred embodiment, the present invention encompasses a method for embolization wherein the crosslinked polyvinylalcohol microspheres being administered in the injectable suspension comprise from about 0.5% to about 20% crosslinked polyvinylalcohol by weight in the hydrogel form. In another embodiment, the present invention encompasses a method for embolization wherein the crosslinked polyvinylalcohol microspheres being administered further comprise a cell adhesion promoter, a marking agent, or both. In still another embodiment, the present invention encompasses a method for embolization wherein the polyvinylalcohol microspheres being administered further comprise an anti-angiogenic agent.

The present invention further encompasses a process for producing crosslinked polyvinylalcohol microspheres, having a diameter ranging from about 10 μm to about 2,000 μm, which comprises: a) dissolving polyvinylalcohol in an acidic solution; b) adding an aldehyde to said polyvinylalcohol-containing solution, or vice verse, to form a mixture; c) adding said mixture, with agitation, to an oil containing from about 0.1% to about 10% of an emulsifier having Hydrophilic-Hydrophobic Balance ("HLB") less than 5, or vice verse, to form an emulsion with droplets of polyvinylalcohol suspended in said oil; d) heating said emulsion to condense said aldehyde on polyvinylalcohol chains and thereby forming spherical particles of crosslinked polyvinylalcohol; e) removing said oil from said spherical particles of crosslinked polyvinylalcohol; f) neutralizing said active aldehyde on said spherical particles of crosslinked polyvinylalcohol; g) washing said neutralized spherical particles of crosslinked polyvinylalcohol with physiological aqueous buffers; and preferably h) sterilizing said washed spherical particles of crosslinked polyvinylalcohol. The polyvinylalcohol-containing solution used in this process preferable has a polyvinylalcohol concentration from about 0.5% to about 20% (w/v).

4. DETAILED DESCRIPTION OF THE INVENTION

Microspheres useful for embolization which comprise polyvinylalcohol, injectable suspensions suitable for embolization which comprise the polyvinylalcohol microspheres, methods for prophylactic or therapeutic embolization using such injectable suspensions, and processes for producing the polyvinylalcohol microspheres are described herein.

As used herein, "microspheres" means solid insoluble particles which may be suspended in biological or biologically-compatible liquids, and which have, under microscopic examination, substantially a sphere or a spheroidal shape (ellipsis). A sphere is defined as a volume that presents the lowest external surface area. The surface of microspheres appear smooth under less than 1000-fold magnifications.

As used herein, "irregular particles" means solid insoluble particles, under microscopic examination, have a shape that is not a substantially sphere or spheroidal (ellipsis). The shape of irregular particles is often the result of a larger solid particle that has been crushed. Each irregular particle appears non-uniform in shape as compared to microspheres. Also in contrast to microspheres, irregular particles have rough surface. The length, thickness and depth of irregular particles are not uniform; they show angles and protuberances on the surface. These particles also appear irregular in their ability to transmit light under microscopic examination, depending on the thickness of the particles at particular locations.

The use of irregular particles in embolization has certain drawbacks. First, spheres are defined by their diameter. Irregular particles can not be defined geometrically except by their whole volume and do not have real dimensions. Therefore, irregular particles can not be accurately sieved to achieve a uniform or even narrow range size distribution. As a result, it is difficult to properly and completely occlude artery lumen using irregular particles because they can not establish complete contact with all the surface of the artery which is cylindrical. In addition, irregular particles sometimes block the catheter lumen depending on their space orientation inside the lumen of a catheter. Moreover, as a result of the rough surface of irregular particles and the possibility that such particles may break as a consequence of attrition phenomena, very small-sized particles can be generated from the irregular particles. When such very small-sized particles are generated during handling or administration in vivo, inadvertent pulmonary embolization, a potentially fatal complication, can occur. Furthermore, irregular particles have large surface area in comparison to their volume. They tend to form clumps or aggregations, which are responsible for catheter clogging and undesired proximal embolization.

In contrast, use of microspheres described herein in embolization has certain advantages. For example, due to their spherical shape or substantially spherical shape, microspheres can properly and completely occlude artery lumen because they can establish complete contact with all the surface of the artery which is cylindrical. In addition, the microspheres of the present invention can be easily calibrated, and samples or suspensions containing these microspheres will not block or clog catheters because they always have the same dimension regardless of their space orientation in the catheter. Moreover, due to their smooth surface, no attrition will occur and small-sized particles will not be generated from the microspheres; thus avoiding the potentially fatal complications, such as pulmonary embolization. Furthermore, microspheres can only interact with each other on a single point and such contact is not enough to induce aggregation by surface interaction.

The invention described herein encompasses microspheres, having a diameter ranging from about 10 µm to about 2,000 µm, useful for embolization which comprises crosslinked polyvinylalcohol. Preferred diameters for the present invention will depend on the type of embolization and can be readily determined by the skilled artisans. The microspheres of the present invention can be in the form of dry powder or hydrogel. In a preferred embodiment, the present invention encompasses microspheres, which comprise in crosslinked and hydrogel form, from about 0.5% to about 20% crosslinked polyvinylalcohol by weight. In other embodiments, the crosslinked polyvinylalcohol microspheres may further comprise one or more of a cell adhesion promoter, a marking agent, or an anti-angiogenic agent.

The present invention also encompasses an injectable suspension suitable for embolization, which comprises crosslinked polyvinylalcohol microspheres, having a diameter ranging from about 10 µm to about 2,000 µm and a suitable liquid carrier. In a preferred embodiment, the crosslinked polyvinylalcohol microspheres in said injectable suspension have a uniform or narrow size range, wherein the difference in diameter between the microspheres is from about 0 µm to about 150 µm, preferably from about 0 µm to about 100 µm. In other embodiments, the present invention encompasses an injectable suspension wherein the microspheres are comprised of from about 0.5% to about 20% crosslinked polyvinylalcohol by weight in the hydrogel form; an injectable suspension wherein the crosslinked polyvinylalcohol microspheres may further comprise a cell adhesion promoter, a marking agent, and an injectable solution wherein the polyvinylalcohol microspheres and an anti-angiogenic agent.

The present invention additionally encompasses a method for prophylactic or therapeutic embolization in a mammal which comprises administering to said mammal in need of such embolization an injectable suspension comprising an effective amount of crosslinked polyvinylalcohol microspheres, having diameters ranging from about 10 µm to about 2,000 µm, and a suitable liquid carrier. In a preferred embodiment, the present invention encompasses a method for therapeutic embolization wherein the polyvinylalcohol microspheres in the injectable suspension being administered comprise from about 0.5% to about 20% crosslinked polyvinylalcohol by weight in the hydrogel form. In other embodiments, the crosslinked polyvinylalcohol microspheres being administered in said method for prophylactic or therapeutic embolization may further comprise one or more of a cell adhesion promoter, a marking agent and an anti-angiogenic agent.

The present invention further encompasses a process for producing crosslinked polyvinylalcohol microspheres, having diameters ranging from about 10 µm to about 2,000 µm. Various acidic solutions, aldehydes, oils, emulsifiers, agitation speeds, heating conditions and oil removing methods can be used in the process as described below. In other embodiments, the present invention encompasses a process for producing crosslinked polyvinylalcohol microspheres further comprising adding a cell adhesion promoter to the acidic polyvinylalcohol solution before adding the aldehyde; a process further comprising absorbing a marking agent into the crosslinked polyvinylalcohol microspheres; and a process further comprising absorbing an anti-angiogenic agent into the crosslinked polyvinylalcohol microspheres.

For clarity of disclosure, and not by way of limitation, the detailed description of the present invention is divided into the subsections which follow.

4.1. Polyvinylalcohol Microspheres

Polyvinylalcohol is a polymer prepared from polyvinyl acetates by replacement of the acetate groups with hydroxyl groups. Examples of other names for polyvinylalcohol include, but are not limited to, Akwa Tears, Elvanol, Gelvatol, Lipuifilm, Mowiol, Polyviol, Sno Tears, Vinarol and Vinol (*The Merck Index*, 12th Ed., Merck & Co., Inc., 1996, p 1308). Such synonyms are encompassed by the present invention. Polyvinylalcohol can be synthesized according to the procedures disclosed in Hermann, Haehnel, *Ber.* 60:1658 (1927); Schildknecht, *Vinyl and Related Polymers* (Wiley, New York, 1952); Staudinger et al., *Ber.* 60:1782 (1927); Prakt, *Chem.*, 155:261 (1940); Marvel, *J. Am. Soc.*, 60:1045 (1938); McDowell, *J. Am. Soc.*, 62:415 (1940); Marvel, *J. Am. Soc.*, 65:1710 (1943); Leeds, Encyclopedia of Chemical Technology (KirkOthmer ed.), 21:353-368 (Wiley-Interscience, New York, 2nd ed., 1970); *Polyvinyl Alcohol* (Finch Ed.), p 640 (Wiley, New York, 1973); and Dunn, *Chem & Ind*. (London), pp 801-806 (1980). Polyvinylalcohol can also be obtained from commercial chemical suppliers such as Aldrich, Fluka and Sigma.

The present invention provides polyvinylalcohol microspheres having one or more of the following characteristics: 1) substantially spherical; 2) substantially uniform in size and shape; 3) will not aggregate by surface interaction; and 4) the diameter of which can easily be calibrated.

Polyvinylalcohol microspheres having a diameter ranging from about 10 µm to about 2,000 µm are also provided in the present invention. The microspheres of the present invention can be in the form of dry powder or hydrogel. In one embodiment, crosslinked hydrogel microspheres of the present invention comprise about 0.5% to about 20% crosslinked polyvinylalcohol by weight.

The present invention also provides crosslinked polyvinylalcohol microspheres which further comprise a cell adhesion promoter, a marking agent or both. Such cell adhesion promoter include, but are not limited to, CM dextran, collagen, DEAE dextran, gelatin, glucosaminoglycans, fibronectin, lectins, polycations, natural biological cell adhesion agents or synthetic biological cell adhesion agents. In a preferred embodiment, the cell adhesion promoter is selected from the group consisting of CM dextran, collagen and DEAE dextran.

The marking agents useful within the present invention include, but are not limited to, dyes, imaging agents and contrasting agents. Examples of chemical dyes that can be used in the present invention, which make possible a direct visualization of the microspheres, include, but are not limited to, Cibacron Blue and Procion Red HE-3B. Examples of imaging agents that can be used in the present invention include, but are not limited to, magnetic resonance imaging agents such as erbium, gadolinium and magnetite. In a preferred embodiment, a magnetite imaging agent, such as ferrofluid, is used. Examples of contrasting agents that can be used in the present invention include, but are not limited to, barium or iodine salts and amino-3-triiodo-2,4,6-benzoic acid. The use and preparation of the above dyes, imaging agents and contrasting agents are disclosed in U.S. Pat. Nos. 5,635,215; 5,648,100; Boschetti, *Biochem-Biophys. Meth.* 19: 21-36 (1989); and Boschetti et al., *Bull. Sec. Chim.* France. 1986 No. 4), the contents of which are incorporated herein by reference.

In the case of barium or magnetite salts, they can be directly introduced in powdered form in the initial polyvinylalcohol solution in the process of preparing polyvinylalcohol microspheres according to the present invention. It is also possible to incorporate such marking agents into the microspheres after their synthesis. This can be done, for example, by grafting of fluorescent markers such as erythrosine or fluorescein or their derivatives (FITC, EITC, and the like).

In another embodiment, the present invention provides crosslinked polyvinylalcohol microspheres further comprising an anti-angiogenic agent.

The anti-angiogenic agents useful within the present invention include, but are not limited to, AGM-1470 (TNP-470), angiostatic steroids, angiostatin, antibodies against $\alpha v\beta 3$, antibodies against bFGF, antibodies against IL-1, antibodies against TNF-$\alpha$, antibodies against VEGF, auranofin, azathioprine, BB-94 and BB-2516, basic FGF-soluble receptor, carboxyamido-trizole (CAI), cartilage-derived inhibitor (CDI), chitin, chloroquine, CM 101, cortisone/heparin, cortisone/hyaluroflan, cortexolone/heparin, CT-2584, cyclophosphamide, cyclosporin A, dexamethasone, diclofenac/hyaluronan, eosinophilic major basic protein, fibronectin peptides, Glioma-derived angiogenesis inhibitory factor (GD-AIF), GM 1474, gold chloride, gold thiomalate, heparinases, hyaluronan (high and low molecular-weight species), hydrocortisonelbeta-cyclodextran, ibuprofen, indomethacin, interferon-alpha, interferon gamma-inducible protein 10, interferon-gamma, IL-1, IL-2, IL-4, IL-12, laminin, levamisole, linomide, LM609, martmastat (BB-2516), medroxyprogesterone, methotrexate, minocycline, nitric oxide, octreotide (somatostatin analogue), D-penicillamine, pentosan polysulfate, placental proliferin-related protein, placental RNase inhibitor, plasminogen activator inhibitor (PAIs), platelet factor-4 (PF4), prednisolone, prolactin (16-kDa fragment), proliferin-related protein, prostaglandin synthase inhibitor, protamine, retinoids, somatostatin, substance P, suramin, SU1O1, tecogalan sodium (05-4152), tetrahydrocortisol-sthrombospondins (TSPs), tissue inhibitor of metalloproteinases (TIMP 1, 2, 3), thalidomide, 3-aminothalidomide, 3-hydroxythalidomide, metabolites or hydrolysis products of thalidomide, 3-aminothalidomide, 3-hydroxythalidomide, vitamin A and vitreous fluids. In another preferred embodiment, the anti-angiogenic agent is selected from the group consisting of thalidomide, 3-aminothalidomide, 3-hydroxythalidomide and metabolites or hydrolysis products of thalidomide, 3-aminothalidomide, 3-hydroxythalidomide. In a preferred embodiment, the anti-angiogenic agent is thalidomide. The above anti-angiogenic agents are disclosed in U.S. Pat. Nos. 5,593,990; 5,629,327; and 5,712,291; Norrby, *APMIS,* 1997, 105:417-437; O'Reilly, *Investigational New Drugs,* 1997, 15:5-13; and *J. Nat'l Cancer Inst.,* 1996, 88(12): 786-788, the contents of which are incorporated herein by reference.

The crosslinked polyvinylalcohol microspheres of the present invention can be stored and maintained in the form of dry powders, or as hydrogel suspended in a suitable liquid carrier.

4.2. Injectable Suspensions Comprising Polyvinylalcohol Microspheres

The present invention provides an injectable suspension suitable for embolization, which comprises microspheres, having diameters ranging from about 10 µm to about 2,000 µm, useful for embolization, and a suitable carrier. Preferably, the injectable suspension is sterile.

The various specific and preferred polyvinylalcohol microspheres that are described in §4.1. can be used in the injectable suspension.

Kits containing a ready made injectable suspension, or the polyvinylalcohol microspheres described in §4.1. above in powder form, and physiologically acceptable carrier liquid(s) or solution(s) that can solubilize the polyvinylalcohol microspheres powders, are included within the present invention. Suitable liquid carriers for use in the injectable suspensions of the present invention include biological liquids or solutions and liquids or solutions which are biologically compatible or physiologically acceptable. Examples of such liquids or solutions include, but are not limited to, aqueous solutions, saline, physiological solutions which contain sugars, and the like. Such kits can also contain cell adhesion promoters, marking agents, or anti-angiogenic agents, or mixtures thereof. Such kits can further contain injection means such as a needle, a catheter, guides, contrast agents, and physiological dyes, such as methylene blue.

4.3. Methods for Embolization Using the Injectable Suspensions Comprising Polyvinylalcohol Microspheres The present invention provides a method for prophylactic or therapeutic, transient or permanent, embolization in a mammal which comprises administering to said mammal in need of such embolization an injectable suspension comprising an effective amount of microspheres, having diameters ranging from about 10 µm to about 2,000 µm, useful for embolization, wherein said microspheres comprise crosslinked polyvinylalcohol. In a preferred embodiment, the mammal being embolized is a human.

The various specific and preferred injectable suspensions comprising the polyvinylalcohol microspheres that are described in §4.1 and §4.2 can be used in the embolization methods of the present invention.

Conditions and disease states that can be prevented or treated by the present embolization methods include, but are not limited to, solid tumors, vascular malformations, and hemorrhagic events or processes. Regarding tumors, the present embolization methods can be used to suppress pain, to limit blood loss occurring during surgical intervention following embolization, or to bring on tumoral necrosis and to either avoid or minimize the necessity of surgical intervention. With respect to vascular malformations, the present embolization methods can be used to normalize the blood flow to "normal" tissues, to aid in surgery and to limit the risk of hemorrhage. For hemorrhagic events or processes, the present embolization methods can be used to reduce blood flow and to promote cicatrization of the arterial opening(s). In addition, the present embolization methods can be used as a pre-surgical treatment in order to decrease the blood flow in blood rich organs (e.g., the liver) prior to surgical intervention. Examples of specific conditions that can be prevented or treated by the present embolization methods include, but are not limited to: uterine tumors or fibroids; small intestinal hemorrhage, such as that associated with stress ulcer; surgical drain; anastomosis; tuberculous ulcer and nonspecific ulcer; symptomatic hepatic arteriovenous malformation (AVM); primary colorectal cancer; hepatocellular carcinomas; liver metastases; bone metastases; melanomas; cancers of the head or neck; and intracranial meningiomas.

The magnitude of a prophylactic or therapeutic dose of the polyvinylalcohol microspheres of the present invention, of course, vary with the nature of the type, location and severity of the condition to be treated and the route of administration. It will also vary according to the age, weight and response of the individual patient. Effective amounts of the polyvinylalcohol microspheres to be used in the embolization methods of the present invention are based on the recommended doses known to those skilled in the art for the various conditions, diseases or disorders.

An effective amount refers to that amount of polyvinylalcohol microspheres sufficient to result in amelioration of symptoms or a prolongation of survival in a patient. Toxicity and therapeutic efficacy of such polyvinylalcohol microspheres can be determined by standard embolization procedures in experimental animals, or that is sufficient to permanently or temporarily occlude the vascular lumen in question.

Any suitable route of administration may be employed for providing the patient with an effective dosage of polyvinylalcohol microspheres of the present invention at the desired target or location. For example, parenteral, subcutaneous, intramuscular, and the like may be employed. A preferred mode of administration is delivery inside targeted arteries via a catheter.

4.4. Processes for Producing Polyvinylalcohol Microspheres

The present invention provides a process for producing crosslinked polyvinylalcohol microspheres, having a diameter ranging from about 10 µm to about 2,000 µm, which comprises: a) dissolving polyvinylalcohol in an acidic solution; b) adding an aldehyde to said polyvinylalcohol-containing solution to form a mixture, or vice verse; c) adding said mixture, with agitation, to an oil containing from about 0.1% to about 10% of an emulsifier having HLB less than 5, or vice verse, to form an emulsion with droplets of polyvinylalcohol suspended in said oil; d) heating said emulsion to condense said aldehyde on polyvinylalcohol chains and thereby forming spherical particles of crosslinked polyvinylalcohol; e) removing said oil from said spherical particles of crosslinked polyvinylalcohol; f) neutralizing said active aldehyde on said spherical particles of crosslinked polyvinylalcohol; g) washing said neutralized spherical particles of crosslinked polyvinylalcohol with physiological aqueous buffers; and optionally h) sterilizing said washed spherical particles of crosslinked polyvinylalcohol. Various acidic solutions, aldehydes, amino-containing agents, oils, emulsifiers, agitation speeds, heating conditions and oil removing methods can be used in the process.

Various preferred reagents and reaction conditions can be used in the process for producing crosslinked polyvinylalcohol microspheres, as skilled artisans will be aware. For example, in step (a), preferred acidic solutions are 0.5 M $H_2SO_4$—NaCl and 1 M HCl. In step (b), the preferred aldehyde is selected from the group consisting of formaldehyde, glyoxal, glutaraldehyde and terephalaldehyde. More preferably, the aldehyde is glutaraldehyde. In step (c): 1) the preferred oil is selected from the group consisting of vegetal oils (e.g., olive oil, corn oil and sunflower oil), mineral oils (e.g., paraffin oil and silicone oil) and non-polar solvents, and more preferably, the oil is a mineral oil such as paraffin oil; and the preferred emulsifier having HLB less than 5 are preferably used in concentrations from about 0.05% to 5%, and can be selected from the group consisting of sorbitan sesquioleate, sorbitan trioleate, sorbitan tristearate, polyethylene sorbitan monostearate, cellulose acetate butyrate and tetradecanol. The agitation speed used in the process of the present invention will depend upon type of agitation equipment being used and the desired size for the microspheres being produced. In step (d) the heating is preferably conducted at about 80° C. for about 6 hours. In step (e) said oil is removed from said spherical particles of crosslinked polyvinylalcohol using extraction agents such as light non-polar solvents, chlorinated solvents, ethyl-ether, and supercritical carbon dioxide, and preferably by extraction with light non-polar solvent or chlorinated solvent, and more preferably, by extraction with methylene chloride. In step (f) said active aldehyde on said spherical particles of crosslinked polyvinylalcohol is preferably neutralized by an amino-containing agent, such as aminoalcohols, e.g., Tris, 2-aminoethanol, aminosorbitol and glucosamine, and more preferably, by a 0.5 M Tris-HCl buffer (pH 9).

In still another embodiment, the present invention provides a process for producing crosslinked polyvinylalcohol microspheres further comprising adding a cell adhesion promoter to the acidic polyvinylalcohol solution before adding the aldehyde. In a preferred embodiment, the cell adhesion promoter is selected from the group consisting of CM dextran, collagen, DEAE dextran, gelatin, glucosaminoglycans, fibronectin, lectins, polycations, natural biological cell adhesion agents or synthetic biological cell adhesion agents. In a more preferred embodiment, the cell adhesion promoter is selected from the group consisting of CM dextran, collagen, and DEAE dextran.

In another embodiment, the present invention provides a process for producing crosslinked polyvinylalcohol microspheres further comprising absorbing a marking agent into the crosslinked polyvinylalcohol microspheres. Preferably, the marking agent is selected from the group consisting of a dye, an imaging agent and a contrasting agent, and more preferably, the marking agent is an imaging agent such as ferrofluid.

In still another embodiment, the present invention provides a process for producing crosslinked polyvinylalcohol microspheres further comprising absorbing an anti-angiogenic agent into the crosslinked polyvinylalcohol microspheres. More preferably, the anti-angiogenic agents described in §4.1 above can be used.

This invention will be more completely described by means of the following examples, which are to be considered illustrative and not limitative.

5. EXAMPLES

Materials

All chemical reagents including polyvinylalcohol are from Aldrich, Europe. All biological reagents such as dextran derivatives, cell adhesion factor, etc. are from Sigma, U.S.A. The agitation system and the sieving machine are from Prolabo, France.

Example 1

Preparation of Crosslinked Microspheres Comprising 5% Polyvinylalcohol

Five grams of polyvinylalcohol are dissolved in 75 ml of a 0.5 M $H_2SO_4$-0.1 M NaCl solution under stirring. The suspension is agitated until a clear solution forms and then 25 ml of formalaldehyde are added to the solution. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of formaldehyde on polyvinylalcohol chains and thus forming spherical particles of crosslinked polyvinylalcohol.

Particle size is managed by the speed of agitation of the emulsion. For example, in order to obtain microspheres with diameter around 300 μm (average dimension), the agitation speed is kept at about 250 rpm.

Hydrogel microspheres of polyvinylalcohol are then collected by filtration. Alternatively, hydrogel microspheres of polyvinylalcohol may be collected by centrifugation or by simple decanting. Residue oil is extracted by non-polar solvents or chlorinated solvents such as methylene chloride. The resulting oil-free microspheres are then treated with a 0.5 M Tris-HCl buffer (pH 9) overnight at room temperature to neutralize excess aldehydes.

Finally, the polyvinylalcohol microspheres are washed with physiological aqueous buffers, sieved to desired diameter, sterilized and stored as liquid suspensions. This material can be used for embolization procedure.

Example 2

Preparation of Crosslinked Microspheres Comprising 20% Polyvinylalcohol

Twenty grams of polyvinylalcohol are dissolved in 75 ml of a 0.5 M $H_2SO_4$-0.1 M NaCl solution under stirring. The suspension is agitated until a clear solution forms and then 25 ml of formalaldehyde are added to the solution. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of formaldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 3

Preparation of Crosslinked Microspheres Comprising 10% Polyvinylalcohol

Ten gram of polyvinylalcohol are dissolved in 75 ml of a 0.5 M $H_2SO_4$-0.1 M NaCl solution under stirring. The suspension is agitated until a clear solution forms and then 25 ml of a 25% aqueous solution of glutaraldehyde are added to the solution. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glutaraldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 4

Preparation of Crosslinked Microspheres Comprising 10% Polyvinylalcohol

Ten gram of polyvinylalcohol are dissolved in 85 ml of a 0.5 M $H_2SO_4$-0.1 M NaCl solution under stirring. The suspension is agitated until a clear solution forms and then 15 ml of a 25% aqueous solution of glyoxal are added to the solution. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glyoxal on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 5

Preparation of Polyvinylalcohol Microspheres Containing Collagen

Ten gram of polyvinylalcohol are dissolved in 75 ml of a 0.5 M $H_2SO_4$-0.1 M NaCl solution under stirring. The suspension is agitated until a clear solution forms. To this solution 10 ml of 2% collagen in water are added under stirring and then 15 ml of a 50% aqueous solution of glutaraldehyde are added. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glutaraldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 6

Preparation of Polyvinyl Alcohol Microspheres Containing DEAE Dextran

Ten gram of polyvinylalcohol are dissolved in 75 ml of a 0.5 M $H_2SO_4$-0.1 M NaCl solution under stirring. The suspension is agitated until a clear solution forms. To this solution 10 ml of 1% DEAE dextran in water are added under stirring and then 15 ml of a 50% aqueous solution of glutaraldehyde are added. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glutaraldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 7

Preparation of Polyvinylalcohol Microspheres Containing CM Dextran

Ten gram of polyvinylalcohol are dissolved in 75 ml of a 0.5 M $H_2SO_4$-0.1 M NaCl solution under stirring. The suspension is agitated until a clear solution forms. To this solution 10 ml of 1% CM dextran in water are added under stirring and then 15 ml of a 50% aqueous solution of glutaraldehyde are added. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glutaraldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 8

Preparation of Polyvinylalcohol Microspheres Containing Collagen and DEAE Dextran Ten gram of polyvinylalcohol are dissolved in 65 ml of a 0.5 M $H_2SO_4$-0.1 M NaCl solution under stirring. The suspension is agitated until a clear solution forms. To this solution 10 ml of 1% DEAE dextran in water and 10 ml of 2% collagen in water are added under vigorous stirring and then 15 ml of a 50% aqueous solution of glutaraldehyde are added. The resulting mixture is rapidly poured into 500 ml of agitated paraffin oil containing 2% of sorbitan sesquioleate. Under these conditions, an emulsion is formed with droplets of polyvinylalcohol in suspension oil. The emulsion is heated at about 80° C. for at least 6 hours to obtain the condensation of glutaraldehyde on polyvinylalcohol chains and thus forming spherical particles of crosslinked polyvinylalcohol.

Particle size control, microspheres collection, oil extraction, neutralization of aldehydes, microspheres wash, sieve and sterilization are conducted as described in Example 1.

Example 9

Preparation of Polyvinylalcohol Microspheres Containing Magnetite

Fifty ml of polyvinylalcohol microspheres obtained according to Examples 1 to 8 are each packed into a 16 mm diameter chromatographic column and washed with a physiological buffer. The column is then loaded with a colloidal suspension of ferrofluid (very small particles of magnetite) at a flow rate of 10 ml/hour. Particles of magnetite are adsorbed by the polyvinylalcohol hydrogel network and permanently trapped. Resulting microspheres are used for regular embolization procedure and can be monitored by MRI.

Example 10

Impregnated Polyvinylalcohol Microspheres with Angiogenesis Inhibitors

Polyvinylalcohol microspheres obtained according to Examples 1 to 8 are dehydrated by sequential washing with ethanol to eliminate water. Ethanol is eliminated by washing with acetone and finally the polyvinylalcohol microspheres are dehydrated under dry nitrogen. An aqueous solution of 10 mg/ml of thalidomide is prepared and 1 gram of dry polyvinylalcohol microspheres is mixed with 12 ml of drug solution. The suspension is gently agitated for 2 hours. Dry microspheres swell while adsorbing the drug in solution.

The resulting microspheres impregnated with the drug are used for a normal embolization procedure.

Example 11

Absorption of Drugs by Ion Exchange on Polyvinylalcohol Microspheres

Polyvinylalcohol microspheres obtained according to Examples 6 and 8 containing about 80 µmol of cationic groups can adsorb anionic molecules by ion exchange. Microspheres are equilibrated with a 10 mM Tris-HCl buffer (pH 7.5) in which the molecule of interest, such as antiangiogenic or anti-inflammatory agents, are previously dissolved. Under these conditions the molecule of interest is adsorbed by ion exchange effect, and the resulting microspheres can be used for regular embolization procedures.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for embolization in a mammal, comprising administering to said mammal microspheres comprising crosslinked polyvinylalcohol, wherein said microspheres (a) have a diameter ranging from about 10 µm to about 2,000 µm, (b) are substantially spherical, (c) are sterile, and wherein any excess aldehydes on said microspheres are neutralized by an aminoalcohol.

2. The method of claim 1, wherein the diameter of said microspheres is in the range from about 50 µm to about 1,000 µm.

3. The method of claim 1, wherein the microspheres are comprised of from about 0.5% to about 20% crosslinked polyvinylalcohol by weight in hydrogel form.

4. The method of claim 1, wherein said microspheres further comprise a cell adhesion promoter.

5. The method of claim 4, wherein the cell adhesion promoter is selected from the group consisting of carboxymethyl (CM) dextran, collagen, DEAE dextran, gelatin, glucosaminoglycans, fibronectin, lectins, and polycations.

6. The method of claim 4, wherein the cell adhesion promoter is selected from the group consisting of CM dextran, collagen and DEAE dextran.

7. The method of claim 4, wherein the cell adhesion promoter is a natural biological cell adhesion promoter.

8. The method of claim 4, wherein the cell adhesion promoter is a synthetic biological cell adhesion promoter.

9. The method of claim 1, wherein said microspheres further comprise a marking agent.

10. The method of claim 9, wherein the marking agent is selected from the group consisting of a dye, an imaging agent and a contrasting agent.

11. The method of claim 1, further comprising an antiangiogenic agent.

12. The method of claim 1, wherein the aminoalcohol is selected from the group consisting of Tris, 2-aminoethanol, aminosorbitol and glucosamine.

13. The method of claim 1, wherein the microspheres are substantially uniform in size.

14. The method of claim 1, wherein the microspheres are substantially uniform in shape.

15. A method for embolization in a mammal, comprising administering to said mammal an injectable sterile suspension comprising:
   (i) microspheres comprising crosslinked polyvinylalcohol, wherein said microspheres (a) have a diameter ranging from about 10 µm to about 2,000 µm, (b) are substantially spherical, (c) are sterile, and wherein any excess aldehydes on said microspheres are neutralized by an aminoalcohol; and
   (ii) a suitable liquid carrier.

16. The method of claim 15, wherein the diameter of the microspheres are in the range from about 50 µm to about 1,000 µm.

17. The method of claim 15, wherein the microspheres are comprised of from about 0.5% to about 20% crosslinked polyvinylalcohol by weight in hydrogel form.

18. The method of claim 15, wherein the microspheres further comprise a cell adhesion promoter.

19. The method of claim 18, wherein the cell adhesion promoter is selected from the group consisting of CM dextran, collagen, DEAE dextran, gelatin, glucosaminoglycans, fibronectin, lectins, and polycations.

20. The method of claim 18, wherein the cell adhesion promoter is selected from the group consisting of CM dextran, collagen and DEAE dextran.

21. The method of claim 18, wherein the cell adhesion promoter is a natural biological cell adhesion promoter.

22. The method of claim 18, wherein the cell adhesion promoter is a synthetic biological cell adhesion promoter.

23. The method of claim 18, wherein the microspheres further comprise a marking agent.

24. The method of claim 23, wherein the marking agent is selected from the group consisting of a dye, an imaging agent and a contrasting agent.

25. The method of claim 15, further comprising an anti-angiogenic agent.

26. The method of claim 15, wherein the aminoalcohol is selected from the group consisting of Tris, 2-aminoethanol, aminosorbitol and glucosamine.

27. The method of claim 15, wherein the microspheres are substantially uniform in size.

28. The method of claim 15, wherein the microspheres are substantially uniform in shape.

\* \* \* \* \*